United States Patent [19] [11] Patent Number: 4,977,177
Bommer et al. [45] Date of Patent: * Dec. 11, 1990

[54] TETRAPYRROLE POLYAMINOMONOCARBOXYLIC ACID THERAPEUTIC AGENTS

[75] Inventors: Jerry C. Bommer, Ogden; Bruce F. Burnham, Logan, both of Utah

[73] Assignee: Nippon Petrochemicals Company, Ltd., Tokyo, Japan

[*] Notice: The portion of the term of this patent subsequent to Apr. 7, 2004 has been disclaimed.

[21] Appl. No.: 728,752

[22] Filed: Apr. 30, 1985

[51] Int. Cl.$^5$ .................... A61K 31/40; A61K 49/00; C07D 487/00
[52] U.S. Cl. .................................. 514/410; 540/145; 424/9
[58] Field of Search .................. 540/145; 560/19, 125; 372/81; 514/427, 41

[56] References Cited

U.S. PATENT DOCUMENTS

| 4,393,071 | 7/1983 | Fujii et al. | 514/10 |
| 4,649,151 | 3/1987 | Dougherty et al. | 540/145 |
| 4,656,186 | 4/1987 | Bommer et al. | 514/410 |
| 4,675,338 | 6/1987 | Bommer et al. | 514/410 |
| 4,693,885 | 9/1987 | Bommer et al. | 540/145 |

FOREIGN PATENT DOCUMENTS

| 0118913 | 9/1984 | European Pat. Off. | 540/145 |
| 0168831 | 7/1985 | European Pat. Off. | |
| 0168832 | 7/1985 | European Pat. Off. | |
| 2809093 | 9/1978 | Fed. Rep. of Germany | |
| 0077280 | 6/1981 | Japan | 540/145 |
| 0000981 | 1/1983 | Japan | 540/145 |
| 8401382 | 4/1984 | PCT Int'l Appl. | |

OTHER PUBLICATIONS

Lautsch et al., Chem. Ber. 90(4): 470–481, 1957.
Grenan, Marie, Tsutsui, Minoru and Wysor, Michael Phototoxicity of the Chemotherapeutic Agents, Hematoporphyrin D, Meso–Tetra(p-sulfophenyl) Porphine and Zinc-Tetra(p-sulfophenyl)porphine Res. Comm. Chem. Path. & Parm. 30(2) 317–327, (1980).
Jackson, Anthony H., Kenner, George W., Smith, Kevin M., and Suckling, Calvin, J. Synthetic Approaches To Versatile Hemoprotein Model Compounds, Built from Porphyrins and Peptides, J. Chem. Soc. Perkin Trans. I, 1441–1448, (1982).
Chemical Berischet, 90, 470–481, 1957 by Lautsch et al., Hoppe-Seyler's Ztschr. Phy Chem. 327, 205–216, 1962, Lossee and Müller.
Chimia, 13, 129–180, 1959, By Karrer Tetrahedron Letters, 23, 2017–2020, 1978, by Pelter, et al.
Current Microbiology 8, 195–199, 1983, by Gauthier, et al., Zhurnal Organicheshoi K111 M11, 15, 828–835, 1979 by Bacunbee, et al.

Primary Examiner—Douglas W. Robinson
Assistant Examiner—Kevin Weddington
Attorney, Agent, or Firm—Scully, Scott, Murphy & Presser

[57] ABSTRACT

This invention relates to new therapeutic compositions which are useful in photodiagnosis and phototherapy, especially in the detection and treatment of tumors and cancerous tissues in the human or animal body. The compounds of the present new therapeutic composition are mono-, di or polyamides of an amino monocarboxylic acid and a tetrapyrrole containing at least one carboxyl group of the structure

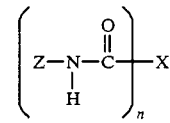

wherein Z is the aminomonocarboxylic acid residue less the amino group, X is the tetrapyrrole residue less the carboxy group, and "n" is an integer from 1 to 4 inclusive.

46 Claims, No Drawings

TETRAPYRROLE POLYAMINOMONOCARBOXYLIC ACID THERAPEUTIC AGENTS

FIELD OF THE INVENTION

This invention relates to new compounds which are useful in photodiagnosis and phototherapy, especially in the detection and treatment of tumors and cancerous tissues in the human or animal body.

DESCRIPTION OF THE PRIOR ART

It is known to irradiate tumors and cancerous tissues in the human body with intensive light following administration of a hematoporphyrin derivative in the wavelength range of 626 to 636 namometers to reduce and, at times, destroy the cancerous cells (see PCT published specification No. WO 83/00811). It is also known that porphyrins, especially the sodium salt of protoporphyrins, can maintain or promote the normal functions of cells and are useful for preventing the genesis, growth, metastasis, and relapse of malignant tumors. Japanese Published Patent Application No. 125737/76 describes the use of porphyrins as tumor.inhibiting agents, exemplifying etioporphyrin, mesoporphyrin, protoporphyrin, deuteroporphyrin, hematoporphyrin, coproporphyrin, and uroporphyrin.

In Tetrahedron Letters No. 23, pp. 2017–2020 (1978), there is described an amino monocarboxylic acid adduct of the pigment bonellin obtained by extraction of principally the body wall of the marine echuroid *B. viridis*. The structure of these adducts is presumed to be an amide formed through either of the free carboxy groups of bonellin and the amino mono-carboxylic acid. Hydrolysis of the adduct yielded a mixture of valine, isoleucine, leucine and alloisoleucine. No use for these amino acid adducts is described in this reference.

That the tetrapyrroles cause intense photosensitivity in animals in well known and has been documented in numerous articles in literature, e.g., J. Intr. Sci. Vitaminol, 27, 521–527 (1981); Agric. Biol. Chem., 46(9), 2183–2193 (1982); Chem. Abst. 98, 276 (1983) and 88 6976m (1928).

SUMMARY OF THE INVENTION

The products contemplated by this invention are cyclic and acyclic tetrapyrroles derived by various procedures from naturally-occurring tetrapyrroles. The cyclic tetrapyrroles have as their common parent tetrapyrrole, uroporphyrinogen, and possess the following ring structure:

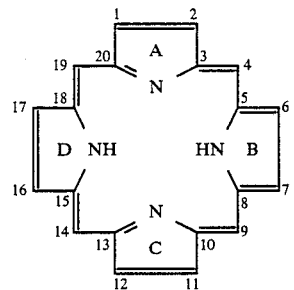

in which the positions in the molecule are numbered 1–20, and the rings identified by letters A, B, C and D, and also include perhydro-, e.g., dihydro- and tetrahydro-, derivatives of the said ring structure, e.g., compounds in which one or more double bonds are absent. There are present in the ring system four pyrrole rings joined through the alpha positions of the respective pyrrole rings by a methine group, i.e., —CH=. The compounds of the present invention are designated as derivatives of the tetrapyrroles for convenience in the disclosure and the appended claims and it will be understood that the term "tetrapyrrole" will designated compounds of the characteristic ring structure designated hereinbefore as well as the corresponding perhydro derivatives, and the corresponding non-cyclic pyrroles, i.e., the linear tetrapyrroles, commonly known as the bile pigments.

The tetrapyrroles employed in the present invention are all derived by various means and various alteration procedures from natural tetrapyrroles. The naturally occurring tetrapyrroles have as their common ancestor uroporphyrinogen III, a hexahydroporphyrin reduced at the bridge positions. For example, synthetic or biosynthetic derivatives or products of protoporphyrins IX or protoporphyrinogen IX are well-known in the art (see, for example, Porphyrins and Metalloporphyrins, K. Smith Elsivier; The Porphyrins (Vols. 1–7) D. Dolphin, Academic Press; and Biosynthetic Pathways, Vol. III, Chapter by B. Burnham, editor D. M. Greenberg, Academic Press).

The non-cyclic tetrapyrroles are commonly known as bile pigments and include, for example, bilirubin and biliverdin. These tetrapyrroles are also derived from protoporphyrin, e.g., as metabolic products in animals.

A further characteristic of the present new compounds is the presence of at least one amide linkage in a substituent at any of the numbered positions of the ring structure. These are present in the instant new compounds together with other substituents as defined hereinafter.

Thus, the present invention contemplates amino acid or peptide derivatives of compounds which contain the chromophore of porphyrins, chlorins or bacteriochlorins, as well as related porphyrin compounds. The peptide linkage involves a carboxy group of the chromophore-bearing compound and the amino group of the specified amino acid. The present new compounds embrace, inter alia, derivatives of the tetrapyrroles which contain a free carboxy group. These derivatives include the major classes of tetrapyrroles: carboxy-containing porphyrins, chlorins, and bacteriochlorins, which are well-known to those skilled in this art.

The amino acid employed in the present invention to form the aforesaid peptide linkage are aminomonocarboxylic acids in which the amino group, of course, is located on a carbon atom of the monocarboxylic acid. The specific position of the amino group in the carbon atom chain is not critical, the only requirement that the amino group be available to form the requisite peptide linkage with the carboxyl group of the selected porphyrin. Thus, a variety of amino monocarboxylic acids are useful in the present invention, including serine, glycine, α-aminoalanine, β-aminoalanine, ε-amino-n-caproic acid, piperidine-2-carboxylic acid, piperidine-6-carboxylic acid, pyrrole-2-carboxylic acid, pyrrole-5-carboxylic acid, piperidine-6-propionic acid, pyrrole-5-acetic acid, and similar such acids. These amino acids may be substituted with angular alkyl groups, such as methyl and ethyl groups, as well as other groups which do not adversely affect the capability of the amino group to form the peptide linkage, e.g., alkoxy groups, or acyloxy groups, and may also include additional amino groups. The preferred amino acids are the naturally occurring α-amino acids, serine, alanine, and glycine, which are readily available and up to the present, have provided the best results.

Exemplary compounds of the tetrapyrrole classes are illustrated in Table I in which the numbered positions of the tetrapyrrole ring structure are used to designate the position of the indicated substituent. The absence of double bonds in the ring system is designated under "dihydro" with each set of numbers (ring position) indicating the absence of a double bond between the designated positions.

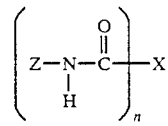

wherein Z is the aminomonocarboxylic acid residue less the amino group and X is the tetrapyrrole residue less the carboxy group and "n" is an integer from 1 to 4 inclusive.

The particularly preferred compounds are fluores-

TABLE I

| PORPHYRIN | Ring Position | | | | | | | | | |
|---|---|---|---|---|---|---|---|---|---|---|
| | A | | B | | C | | | D | | |
| | 1 | 2 | 6 | 7 | 11 | 12 | 14 | 16 | 17 | Dihydro |
| Coproporphyrin III | Me | Pr | Me | Pr | Me | Pr | H | Pr | Me | — |
| Deuteroporphyrin IX | Me | H | Me | H | Me | Pr | H | Pr | Me | — |
| Hematoporphyrin IX | Me | Me<br>–CH<br>OH | Me | Me<br>–CH<br>OH | Me | Pr | H | Pr | Me | — |
| Protoporphyrin IX | Me | V | Me | V | Me | Pr | H | Pr | Me | — |
| Photoprotoporphyrin IX (one of two isomers shown) | Me | V | {–Me<br>–OH | =CHCHO | Me | Pr | H | Pr | Me | 6,7 |
| Mesoporphyrin IX | Me | Et | Me | Et | Me | Pr | H | Pr | Me | — |
| Transmesochlorin IX | Me | {H<br>Me | {H<br>Et | Me | Et | Me | Pr | H | Pr | Me | 1,2 |
| Transmesochlorin IX | Me | Et | {H<br>Me | {H<br>Et | Me | Pr | H | Pr | Me | 6,7 |
| Chlorin e4 | Me | V | Me | Et | Me | CO2H | Me | {H<br>Pr | {H<br>Me | 16,17 |
| Chlorin e6 | Me | V | Me | Et | Me | CO2H | Ac | {H<br>Pr | {H<br>Me | 16,17 |
| Mesochlorin e4 | Me | Et | Me | Et | Me | CO2H | Me | {H<br>Pr | {H<br>Me | 16,17 |
| Isochlorin e4 | Me | V | Me | Et | Me | H | Ac | {H<br>Pr | {H<br>Me | 16,17 |
| Mesoisochlorin e4 | Me | Et | Me | Et | Me | H | Ac | {H<br>Pr | {H<br>Me | 16,17 |
| Mesochlorin e6 | Me | Et | Me | Et | Me | CO2H | Ac | {H<br>Pr | {H<br>Me | 16,17 |
| Bacteriochlorin e6 | Me | ACL | {H<br>Me | {H<br>Et | Me | CO2H | Ac | {H<br>Pr | {H<br>Me | 6,7<br>16,17 |
| Bacteriochlorin e4 | Me | ACL | {H<br>Me | {H<br>Et | Me | CO2H | Me | {H<br>Pr | {H<br>Me | 6,7<br>16,17 |
| Bacterioisochlorin e4 | Me | ACL | {H<br>Me | {H<br>Et | Me | H | Ac | {H<br>Pr | {H<br>Me | 6,7<br>16,17 |

Notes:
Me: —CH3 (Methyl group)
Pr: —CH2CH2COOH (Propionic acid group)
V: —CH=CH2 (Vinyl group)
Et: —CH2CH3 (Ethyl group)
Ac: —CH2COOH (Acetic acid group)
ACL: CH3—CO— (Acetyl group)

The present new compounds are mono, di- or polyamides of an aminomonocarboxylic and a tetrapyrrole containing at least one carboxyl group of the structure cent mono, di, tri, or polyamides of an aminomonocarboxylic acid and a tetrapyrrole compound of the formula:

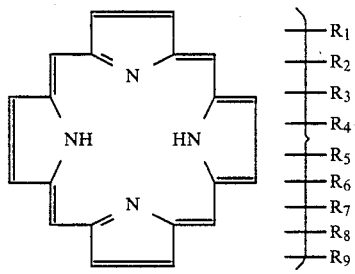

or the corresponding di- or tetrahydrotetrapyrroles wherein $R_1$ is methyl;

$$\begin{pmatrix} -H \\ -CH_3 \end{pmatrix} \text{ or } \begin{pmatrix} -OH \\ -CH_3 \end{pmatrix};$$

$R_2$ is H, vinyl, ethyl, $$\begin{array}{c} -CHCH_3, \\ | \\ OH \end{array}$$

acetyl, $$\begin{pmatrix} -H, & \overset{H}{\underset{|}{-C=O,}} \\ -\text{ethyl}, & \end{pmatrix}$$

$CH_2CH_2CO_2H$, or $=CHCHO$;

$R_3$ is methyl $$\begin{pmatrix} -H \\ -CH_3 \end{pmatrix} \text{ or } \begin{pmatrix} -CH_3; \\ -OH \end{pmatrix}$$

$R_4$ is H, vinyl, ethyl, $$\begin{array}{c} -CHCH_3, \\ | \\ OH \end{array}$$

$CH_2CH_2CO_2H$, $=CHCHO$; or $$\begin{pmatrix} -H \\ -\text{ethyl}; \end{pmatrix}$$

$R_5$ is methyl;
$R_6$ is H, $CH_2CH_2CO_2H$, $CH_2CH_2CO_2R$ or $CO_2H$;
$R_7$ is $CH_2CH_2CO_2H$, $CH_2CH_2CO_2R$, or $$\begin{pmatrix} -CH_2CH_2CO_2H; \\ -H \end{pmatrix}$$

$R_8$ is methyl or $$\begin{pmatrix} -CH_3 \\ -H \end{pmatrix}$$

$R_9$ is H, COOH, $CH_2COOH$ or methyl; provided that when $R_1$, $R_2$, $R_3$, $R_4$, $R_7$ and $R_8$ represent two substituents or are divalent and attached to the same carbon, the respective pyrrole ring to which attached is a dihydropyrrole;

R is lower alkyl or benzyl; with the proviso that at least two of $R_1$–$R_9$ include a free carboxyl group; and salts thereof.

Another preferred embodiment of the present invention is the fluorescent mono, di, tri or polyamide of an aminomonocarboxylic acid and a tetrapyrrole compound of the formula:

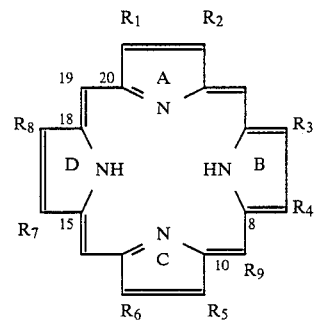

or the corresponding di- or tetrahydratetrapyrroles wherein $R_1$, $R_2$, $R_3$, $R_4$, $R_5$, $R_6$, $R_7$, $R_8$ and $R_9$ are as defined heretofore.

The preferred tetrapyrrole carboxylic acids are those wherein at least three carboxylic acid groups are present in the tetrapyrrole, preferably asymmetrically attached to the porphyrin ring system, e.g., the carboxylic acid groups are present on the rings A and B side of the molecule or on the rings D and C side of the molecule.

The particularly preferred compounds of this invention are those represented by the formula:

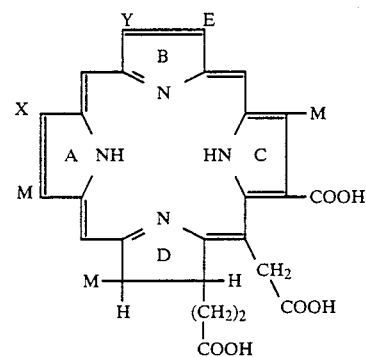

wherein;
X=H, vinyl, ethyl, acetyl or formyl;
Y=methyl or formyl;
M=methyl; and
E=ethyl and pharmaceutically-acceptable salts thereof.

The present new compounds form salts with either acids or bases. The acid salts are particularly useful for purification and/or separation of the final amide products as are the salts formed with bases. The base salts, however, are particularly preferred for diagnostic and therapeutic use as hereindescribed.

The acid salts are formed with a variety of acids such as the mineral acids, hydrochloric, hydrobromic, nitric and sulfuric acids, organic acids such as tolunesulfonic and benzenesulfonic acids.

The base salts include, for example, sodium, potassium, calcium, magnesium, ammonium, triethylammonium, trimethylammonium, morpholine and piperidine salts and similar such salts.

The acid and base salts are formed by the simple expediency of dissolving the selected amino acid tetrapyrrole amide in an aqueous solution of the acid or base and evaporation of the solution to dryness. The use of a water-miscible solvent for the amide can assist in dissolving the amide.

The final amide products can also be converted to metal complexes for example by reaction with metal salts. The magnesium complexes may be useful for the same purpose as the adduct product. Other metal complexes, as well as the magnesium complex, including, for example, iron and zinc, are useful to preclude contamination during processing of the adduct product by metals such as nickel, cobalt and copper, which are difficult to remove. Zinc and magnesium are readily removed from the final adduct product after processing is completed.

Since many of the aminomonocarboxylic acids exist in both the D- and L-forms, and also are employed in mixtures of these forms as well as the D, L-form, the selection of the starting amino acid will, of course, result in products in which the respective isomer or mixture of isomers exist. The present invention contemplates the use of all such isomers, but the L-form is particularly preferred.

The present new compounds are prepared by the usual peptide synthetic routes which generally include any amide-forming reaction between the selected amino acid and the specific tetrapyrrole. Thus, any amide-forming derivative of the tetrapyrrole carboxylic acid can be employed in producing the present new peptides, e.g., lower alkyl esters, anhydrides and mixed anhydrides.

The preferred preparative methods use mixed anhydrides of the carboxylic acid or carbodiimides. The reactants are merely contacted in a suitable solvent therefor and allowed to react. Temperatures up to the reflux temperature can be used, with the higher temperatures merely reducing the reaction time. However, excessively high temperatures are usually not preferred so as to avoid unwanted secondary reactions.

The procedures for forming the instant peptides are well known in this art and are provided in detail in the accompanying examples.

Since the selected tetrapyrrole contains more than one carboxyl group, mixtures of products can be formed including isomeric di- and even tri- or higher peptide products, depending on the number of carboxyl groups and depending on the selected stoichiometry. Thus, when equivalent mixtures of amino acid and tetrapyrrole are reacted, the product may contain some monopeptides, but also present will be di- or polypeptides. It is generally possible to separate the monopeptides and higher peptides using known chromatographic techniques. However, such separations are not necessary since the mixed peptides are usually comparable to the separated products in their ultimate use. Thus, mixtures of mono, di, and tri- peptides of the same tetrapyrrole can be used.

Usually, unreacted tetrapyrrole is separated from the peptide products of the invention during purification as, for example, by chromatographic techniques.

Photodiagnosis and Phototherapy

The compounds of the present invention are useful for the photodiagnosis and phototherapy of tumor, cancer and malignant tissue (hereinafter referred to as "tumor").

When a man or animal having tumor is treated with doses of a compound of the present invention and when appropriate light rays or electromagnetic waves are applied, the compound emits light, i.e., fluorescence. Thereby the existence, position and size of tumor can be detected, i.e., photodiagnosis.

When the tumor is irradiated with light of proper wavelength and intensity, the compound is activated to exert a cell killing effect against the tumor. This is called "phototherapy".

Compounds intended for photodiagnosis and phototherapy ideally should have the following properties:

(a) non-toxic at normal therapeutic dosage unless and until activated by light;

(b) should be selectively photoactive;

(c) when light rays or electromagnetic waves are applied, they should emit characteristic and detectable fluorescence;

(d) when irradiated with light rays or electromagnetic waves are applied, they are activated to an extent to exert a cell killing effect against tumor; and (e) easily metabolized or excreted after treatment.

In accordance with testing up to the present, the present new compounds have the foregoing properties and are also characterized by reasonable solubility in saline at physiological pH.

The present new compounds possess greater fluorescence in tumors than do the corresponding basic tetrapyrroles. Their use provides the best contrast in tumors compared to normal tissue around the tumor. The instant compounds absorb activating energy for phototherapy in the convenient range of 600 to 800 nanometers, with the preferred compounds absorbing in the 620–760 nanometer range, i.e., light of longer wavelengths which more readily permits penetration of energy into the tumor for phototherapeutic purpose.

In present experience, the present compounds more uniformly distribute throughout the tumor than the basic tetrapyrrole permitting the use of considerably lower dosage (to about 1/10th of the required normal dose of the basic tetrapyrrole) which lessens, if not eliminates, photosensitization in the host. They also possess a more consistent fluorescence whereas some of the corresponding tetrapyrroles show inconsistent fluorescence or the fluorescence varies from day to day in the host.

A particularly advantageous property of the present compounds resides in the ease with which they are excreted by the host. Generally, within 48 to 72 hours of intravenous or intraperitoneal administration, there are little or no detectable amounts in normal muscle tissue. The present compounds which are excreted with their chromophore intact are recovered from the feces of the host within 48–72 hours of injection. Under equivalent circumstances, substantial amounts of the corresponding tetrapyrroles remain, as compared with only minor amounts of peptides formed with the aminocarboxylic acids remain in the host, e.g., up to about 20%. This property is extremely important in that it contributes to minimization of photosensitization of the host.

The instant compounds can be used for diagnosis and therapeutic treatment of a broad range of tumors. Examples of tumors are gastric cancer, enteric cancer, lung cancer, breast cancer, uterine cancer, esophageal cancer, ovarian cancer, pancreatic cancer, pharyngeal cancer, sarcomas, hepatic cancer, cancer of the urinary bladder, cancer of the upper jaw, cancer of the bile duct, cancer of the tongue, cerebral tumor, skin cancer, malignant goiter, prostatic cancer, cancer of the parotid gland, Hodgkin's disease, multiple myeloma, renal cancer, leukemia, and malignant lymphocytoma. For diagnosis, the sole requirement is that the tumor be capable of selectivity fluorescing when exposed to proper light. For treatment, the tumor must be penetrable by the activation energy. For diagnosis, light of shorter wavelength is used whereas for therapeutic purposes light of longer wavelength is used to permit ready penetration of the tumor tissue. Thus, for diagnosis, light of from 360–760 nanometers can be used, and for treatment, from 620–760, depending on the individual characteristics of the tetrapyrrole. The absorption characteristics of the present new compounds are substantially the same as the tetrapyrrole from which derived.

It is necessary that the light rays be so intense as to cause the compounds to emit fluorescence for diagnosis and to exert a cell killing effect for therapy.

The source of irradiation for photodiagnosis and phototherapy is not restricted, however, but the laser beam is preferable because intensive light rays in a desired wavelength range can be selectively applied For example, in photodiagnosis, the compound of the invention is administered to a human or animal body, and after a certain period of time, light rays are applied to the part to be examined. When an endoscope can be used for the affected part, such as lungs, gullet, stomach, womb, urinary bladder or rectum, it is irradiated using the endoscope, and the tumor portion selectively emits fluorescence. This portion is observed visually, or observed through an adapted fiber scope by eye or on a CRT screen.

In phototherapy, after administration of the dosage, the irradiation is carried out by laser beams from the tip of quartz fibers. Besides the irradiation of the surface of tumor, the internal part of the tumor can be irradiated by inserting the tip of quartz fibers into the tumor. The irradiation can be visually observed or imaged on a CRT screen.

For photodiagnosis, light of wavelengths between 360 and 760 nm. is suitable for activating the present tetrapyrrole compounds. Of course, each compound has a specific optimal wavelength of activation. A long wavelength ultraviolet lamp is particularly suitable for photodiagnosis. Similar methods for viewing of the treated tumor can be used as already described for phototherapy.

The dosages of the present new compounds will vary depending on the desired effect, whether for diagnosis or for treatment. For diagnosis, doses of as little as 1 mg/kg will be effective, and up to about 20 mg/kg can be used. For treatment, the dose will usually approximate about 0.5 mg/kg. Of course, the dosage for either diagnosis or treatment can be varied widely in view of aforesaid advantageous properties of the present compounds, e.g., the ease of elimination from the host, for one The present compounds are apparently non-toxic at the dosage levels employed for diagnosis or treatment. No mortality of test animals due the present compounds has been noted in studies employing dosage levels up to 20 mg/kg.

For both diagnosis and treatment, the present compounds can be administered by the oral, intravenous, or intramuscular routes. They can be formulated as lyophilized sterile, pyrogen-free compounds, preferably in the form of basic salts, e.g., sodium salt The preferred dosage forms are provided as injectable solutions (isotonic).

The irradiation source used in treatment of tumors containing compounds of this invention is a filtered, highintensity, continuous source or pumped dye, or other laser and light delivery system, which is capable of performing within the following limits power intensity 20–500 mw/cm$^2$ at wavelengths between 620 and 760 nm. and a total output of at least 500 mw. or greater. Several currently commercially available lasers meet these criteria.

The tetrapyrroles can be prepared by various synthetic methods which are found in the literature, e.g., Pheophorbides Willstatter, R., Stoll, A.; *Investigations on Chlorophyll*, (Transl. Schertz, FM.M., Merz, A. R.) p. 249. Science Printing Press, Lancaster, Pa., 1928.

Pennington, F. C. Strain, H. H., Svec, W. A., Katz, J. J.; *J. Amer. Chem. Soc.*, 86, 1418 (1964).

Chlorin e$_6$

Willstatter, R. Stoll, A.; *Investigations on Chlorophvll*, (Trans., Schertz, F. M., Merz, A. R.,) p. 176. Science Printing Press, Lancaster, Pa., 1928.

Willstatter, R., Isler, M.; *Ann. Chem.*, 390, 269 (1912).

Fisher, H., Baumler, R.; *Ann Chem.*, 474, 65 (1929).

Fisher, H., Siebel, H.; *Ann. Chem.*, 499, 84 (1932).

Conant, J. B., Mayer, W. W.; *J. Amer. Chem. Soc*, 52, 3013 (1930).

Chlorin e$_4$

Fisher, H., Heckmaier, J., Plotz, E.; *Justus Leibigs Ann. Chem.*, 500,215 (1933).

Chlorin e$_6$, e$_4$, isochlorin e$_4$, mesocchlorin e$_6$, bacteriopheophorbide, bacteriochlorin e$_6$

*Fischer and Orth, "Des Chemie des Pyrrole" Akademische Verlazsgesellschaft, Leipzio,* 1940, Vol II, Part 2.

General Reference for Porphyrins

"Porphyrins and Metalloporphyrins" ed. Kevin M. Smith, Elsevier 1975 N.Y.

The compounds of the present invention can be administered to the host in a variety of forms adapted to the chosen route of administration, i.e., orally, intravenously, intramuscularly or subcutaneous routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and. preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The present new compounds may also be applied directly to tumors, whether internal or external, in the host in topical compositions. Exemplary compositions include solutions of the new compounds in solvents, particularly aqueous solvents, most preferably water. Alternatively, for topical application particularly to skin tumors, the present new compounds may be dispersed in the usual cream or salve formulations commonly used for this purpose or may be provided in the form of spray solutions or suspensions which may include a propellant usually employed in aerosol preparations.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of tumors in living subjects.

The following examples further illustrate the invention.

Mono-, di and Triamides

EXAMPLE 1

Di and mono(DL) serinyl mesoporphyrin IX (mixed anhydrides method)

400 mg (0.0007 moles) of mesoporphyrin IX was suspended in 50 ml of tetrahydrofuran (THF). 360 μl (0.0035 moles) of triethylamine was added with stirring. After 10 minutes, 340 μl (0.0031 moles) ethyl chloroformate was added. After stirring 10 minutes, 10 ml (0.01 moles) of 1M KOH containing 761 mg (0.0072 moles) of DL serine was added to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatrogram.

After checking for product, the solution was adjusted to pH 7.5–8.0 and placed on a reverse phase (C-18 silica) column 2.5×30 cm. The reaction mixture was resolved using a linear gradient of 20-70% methanol in 0.01M KPO$_4$ buffer pH 6.85 (1 liter total volume).

The column effluent was collected via fraction collector and the tube contents were pooled according to individual components. The order of elution was di-DL-serinyl mesoporphyrin IX, mono-DL-serinyl mesoporphyrin IX and unsubstituted mesoporphyrin IX.

The methanol was flashed off and the material was precipitated at pH 2.5-3.0. The ppt. was washed 3 times with dilute acetic acid in water. The product was dried under vacuum. The yield of di (DL) serinyl mesoporphyrin IX was 95.6 mg.

EXAMPLE 2

Di and mono glycyl mesoporphyrin IX (mixed anhydride method)

100 mg (0.000175 moles) of mesoporphyrin IX was suspended in 100 ml of tetrahydrofuran (THF). 360 μl (0.0035 moles) of triethylamine was added with stirring. After 10 minutes, 340 μl (0.0031 moles) of ethylchloroformate was added. After stirring 10 minutes, 10 ml (0.01 moles) of 1M KOH containing 500 mg (0.0066 moles) of glycine was added to the THF solution. This mixture was stirred 60 minutes at room temperature.

The organic solvent was flashed off and the reaction mixture was checked by silica TLC for product. Benzene/methanol/88% formic acid (8.5/1.5/0/13) was used to develop the chromatogram.

After checking for product, the solution was adjusted to pH 7.5-8.0 and placed on a reverse phase (C-18 silica) column 2.5×30 cm. The reaction mixture was resolved using a linear gradient of zero to 50% methanol in 0.01M KPO$_4$ buffer pH 6.85 (1 l total volume).

The column effluent was collected in a fraction collector and the contents were sorted according to individual components. The order of elution was diglycyl mesoporphyrin IX, monoglycyl mesoporphyrin IX and unsubstituted mesoporphyrin IX.

The methanol was flashed off and the material was precipitated at pH 2.5-3.0. The ppt. was washed 3 times with dilute acetic acid in water. The product was dried under vacuum.

EXAMPLE 3

Di and Mono α(DL) alanyl mesoporphyrin IX (mixed anhydride method)

100 mg (0.0007 moles) of mesoporphyrin IX was suspended in 100 ml of tetrahydrofuran (THF). 210 μl (0.002 moles) of triethylamine was added with stirring. After 10 minutes 195 μl (0.00177 moles) of ethylchloroformate was added. After stirring 10 minutes, 10 ml (0.01 moles) of 1M KOH containing 500 mg (0.0056 moles) of α(DL) alanine was added to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatogram.

After checking for product, the solution was adjusted to pH 7.5-8.0 and placed on a reverse phase (C-18 silica) column 2.5×30 cm. The reaction mixture was resolved using a linear gradient of 20-70% methanol in 0.01M KPO$_4$ buffer pH 6.85 (1 l total volume).

The column effluent was collected via fraction collection and the tube contents were sorted according to individual components. The order of elution was di-α(DL) alanyl mesoporphyrin IX, mono-α(DL)-alanyl mesoporphyrin IX and unsubstituted mesoporphyrin IX.

The methanol was flashed off and the material was precipitated at pH 2.5-3.0. The ppt. was washed 3 times with dilute acetic acid in water. The product was dried under vacuum.

EXAMPLE 4

Di and mono βalanyl mesoporphyrin IX (mixed anhydride method)

400 mg (0.0007 moles) of mesoporphyrin IX was suspended in 100 ml of tetrahydrofuran (THF). 360 μl (0.0035 moles) of triethylamine was added with stirring. After 10 minutes, 340 μl (0.0031 moles) ethyl chloroformate was added. After stirring 10 minutes, 10 ml (0.01 moles) of 1M KOH containing 400 mg (0.0044 moles) of βalanine was added to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatogram.

After checking for product, the solution was adjusted to pH 7.5-8.0 and placed on a reverse phase (C-18 silica) column 2.5′30 cm. The reaction mixture was resolved using a linear gradient of 40-80% methanol in 0.01M KPO$_4$ buffer pH 6.85 (1 l total volume).

The column effluent was collected via fraction collector and the tube contents were pooled according to individual components. The order of elution was di-β-alanyl mesoporphyrin IX, mono-β-alanyl mesoporphyrin IX, and unsubstituted mesoporphyrin IX.

The methanol was flashed off and the material was precipitated at pH 2.5-3.0. The ppt. was washed 3 times with dilute acetic acid in water. The product was dried under vacuum. The yield for di-β-alanyl mesoporphyrin IX was 40 mg; the yield for mono-β-alanyl mesoporphyrin IX was 23 mg.

EXAMPLE 5

Di and mono ε amino-n-caproyl mesoporphyrin IX (mixed anhydride method)

400 mg (0.0007 moles) of mesoporphyrin IX was suspended in 50 ml of tetrahydrofuran (THF). 360 μl (0.0035 moles) of triethylamine was added with stirring. After 10 minutes, 340 μl (0.0031 moles) of ethylchloroformate was added. After stirring 10 minutes, 10 ml (0.01 moles) of 1M KOH containing 543 mg (0.00414 moles) of ε-amino-n-caproic acid was added to the THF solution. This mixture was stirred 60 minutes at room temperature.

The organic solvent was flashed off and the reaction mixture was checked by silica TLC for product. Benzene/methanol/88% formic acid (8.5/1 5/0.13) was used to develop the chromatogram.

After checking for product, the solution was adjusted to pH 7.5-8.0 and placed on a reverse phase (C-18 silica) column 2.5×30 cm. The reaction mixture was resolved using a linear gradient of 20-70% methanol in 0.01M KPO$_4$ buffer pH 6.85 (1l total volume).

The column effluent was collected via fraction collector and the tube contents were pooled according to individual components. The order of elution was di-ε-amino-n-caproyl mesoporphyrin IX, mono-ε-amino-n-caproyl mesoporphyrin IX, and unsubstituted mesoporphyrin IX.

The methanol was flashed off and the material was precipitated at pH 2.5–3.0. The ppt. was washed three times with dilute acetic acid in water. The product was dried under vacuum. The yield of di-$\epsilon$-amino-n-caproyl mesoporphyrin IX was 237 mg.

EXAMPLE 6

Di and mono-$\beta$-alanyl Hematoporphyrin IX (mixed anhydride method)

400 mg (0.00059 moles) Hematoporphyrin IX dihydrochloride was suspended in 50 ml of tetrahydrofuran (THF).

360 $\mu$l (0.0035 moles) of triethylamine was added with stirring. After 10 minutes, 340 $\mu$l (0.0031 moles) of ethyl chloroformate was added. After stirring 10 minutes, 10 ml (0.01 moles) of 1M KOH containing 400 mg (0.0044 moles) of $\beta$ alanine was added to the THF solution. This mixture was stirred 60 minutes at room temperature.

The organic solvent was removed by flash evaporation, keeping the temperature below 50° C. The reaction mixture was checked for product by silica TLC using Benzene/methanol/88% formic acid (8.5/1.5/0.13) as solvent to develop the chromatogram.

The solution was adjusted to pH 7.5–8.0 with HCl and placed on a reverse phase (C-18 silica) column 2.5×30 cm.

The mixture was resolved using a linear gradient of 40–80% methanol in 0.01M KPO$_4$ buffer pH 6.85 (1 liter total volume). The individual components were collected as they came off the column in the order di-$\beta$-alanyl hematoporphyrin IX, mono-$\beta$-alanyl hematoporphyrin IX and hematoporphyrin IX.

The methanol was removed from each component by flash evaporation and the material was precipitated by adjusting the pH to 2.5–3.0 using HCl. The precipitate was washed three times with dilute acetic acid in water at the centrifuge and the products dried under vacuum. The yield of di-$\beta$-alanyl hematoporphyrin IX was 52 mg and of mono-$\beta$-alanyl hematoporphyrin was 30 mg.

EXAMPLE 7

Di-L-$\alpha$-Serinyl chlorin $e_6$ (mixed anhydride method)

650 mg chlorin $e_6$ was dissolved in 30 ml of dimethylformamide (DMF). 277 $\mu$l (0.002 moles) of triethylamine was added to the DMF solution. After stirring for five minutes, 201 ul (0.002 moles) of ethyl chloroformate was added and stirring was continued for an additional 30 minutes. 0.95 g (0.009 moles) of L-$\alpha$-serine was added to the DMF solution and allowed to stir for one hour at 50°–60° C.

The DMF solution was checked for product formation by reverse phase (C-18 silica) TLC using methanol/0.01M sodium phosphate buffer, pH 6.85, (7.0/3.0) to develop the chromatogram. The DMF solution was flash evaporated to near dryness and the reaction mixture was then taken up in dilute NaOH and the pH was adjusted to 2.5–3.0 to precipitate out the mixture. The precipitate was then centrifuged down and washed twice with diluted acetic acid in water. The precipitate was then centrifuged down and washed twice with diluted acetic acid in water. The precipitate was then redissolved in dilute NaOH and the pH adjusted to 7.0. This was applied to a reverse phase (C-18 silica) column 3.7 cm×45 cm.

The product was eluted from the column with a solution of 0.01M sodium phosphate buffer, pH 6.85/methanol (7.0/3.0). Fractions were collected and the fractions of pure di-L-$\alpha$-serinyl chlorin $e_6$ were pooled. The methanol was flashed off and the product was precipitated at pH 2.5–3.0. The precipitate was centrifuged down, washed three times with dilute acetic acid, and dried under vacuum. The yield was 200 mg of di-L-$\alpha$-serinyl chlorin $e_6$.

Utilizing the aforementioned carbodiimide or the mixed anhydride methods, the following preferred compounds of this invention can be synthesized:

Chlorin Derivatives

Di - (DL)-serinyl-trans-mesochlorin IX
Di - glycyl-trans-mesochlorin IX
Di - $\alpha$-(DL)-alanyl-trans-mesochlorin IX
Di -$\beta$-alanyl-trans-mesochlorin IX
Di -$\epsilon$-amino-n-caproyl-mesochlorin IX
Di, tri- (D,L)-serinyl chlorin $e_6$
Di, tri- (D,L)-serinyl mesochlorin $e_6$
Di, tri- glycyl chlorin $e_6$
Di, tri- glycyl mesochlorin $e_6$
Di, tri- $\alpha$-(D,L)-alanyl chlorin $e_6$
Di, tri-$\alpha$-(D,L)-alanyl mesochlorin $e_6$
Di, tri- $\beta$-alanyl chlorin $e_6$
Di, tri- $\beta$-alanyl mesochlorin $e_6$
Di, tri- $\epsilon$-amino-n-caproyl chlorin $e_6$
Di, tri-$\epsilon$-amino-n-caproyl mesochlorin $e_6$
Di- (D,L)-serinyl chlorin $e_4$
Di- (D,L)-serinyl mesochlorin $e_4$
Di- (D,L)-serinyl isochlorin $e_4$
Di- (D,L)-serinyl mesoisochlorin $e_4$
Di- glycyl chlorin $e_4$
Di- glycyl mesochlorin $e_4$
Di- glycyl isochlorin $e_4$
Di- glycyl mesoisochlorin $e_4$
Di- $\alpha$-(DL)-alanyl chlorin $e_4$
Di- $\alpha$-(DL)-alanyl mesochlorin $e_4$
Di- $\alpha$-(DL)-alanyl isochlorin $e_4$
Di- $\alpha$-(DL)-alanyl mesoisochlorin $e_4$
Di-$\beta$-alanyl chlorin $e_4$
Di-$\beta$-alanyl mesochlorin $e_4$
Di-$\beta$-alanyl isochlorin $e_4$
Di-$\beta$-alanyl mesoisochlorin $e_4$
Di- $\epsilon$-amino-n-caproyl chlorin $e_4$
Di- $\epsilon$-amino-n-caproyl mesochlorin $e_4$
Di-$\epsilon$-amino-n-caproyl isochlorin $e_4$
Di- $\epsilon$-amino-n-caproyl mesoisochlorin $e_4$
Di- (D,L)-serinylphotoprotoporphyrin IX
Di- glycylphotoprotoporphyrin IX
Di-$\alpha$-(D,L)-alanylphotoprotoporphyrin IX
Di-$\beta$-alanylphotoprotoporphyrin IX
Di-$\epsilon$-amino-n-caproylphotoprotoporphyrin IX

Porphyrin Derivatives

Di- (D,L)-serinylmesoporphyrin IX
Di- glycylmesoporphyrin IX
Di-$\alpha$-(DL)-alanylmesoporphyrin IX
Di-$\beta$-alanylmesoporphyrin IX
Di-$\epsilon$-amino-n-caproylmesoporphyrin IX
Di-(D,L)-serinylprotoporphyrin IX
Di-glycylprotoporphyrin IX
Di-$\alpha$-(D,L)-alanylprotoporphyrin IX
Di-$\beta$-alanylprotoporphyrin IX
Di-$\epsilon$-amino-n-caproylprotoporphyrin IX Di-(D,L)-serinyldeuteroporphyrin IX
Di-glycyldeuteroporphyrin IX
Di-α-(D,L)-alanyldeuteroporphyrin IX
Di-β-alanyldeuteroporphyrin IX
Di-ε-amino-n-caproyldeuteroporphyrin IX
Di, tri, tetra- (D,L)-serinylcoproporphyin III
Di, tri, tetra- glycylcoproporphyrin III
Di, tri, tetra-α-(D,L)-alanylcoproporphyrin III
Di, tri, tetra-β-alanylcoproporphyrin III
Di, tri, tetra-ε-amino-n-caproylcoproporphyrin III
Di-(D,L)-serinylhematoporphyrin IX
Di-glycylhematoporphyrin IX
Di-α-(D,L)-alanylhematoporphyrin IX
Di-β-alanylhematoporphyrin IX
Di-ε-amino-n-caproylhematoporphyrin IX Bacteriochlorin Derivatives Di-(D,L)-serinylbacteriochlorin $e_4$
Di-glycylbacteriochlorin $e_4$
Di-α-(DL)-alanylbacteriochlorin $e_4$
Di-β-alanylbacteriochlorin $e_4$
Di-ε-amino-n-caproylbacteriochlorin $e_4$
Di-(D,L)-serinylbacterioisochlorin $e_4$
Di-glycylbacterioisochlorin $e_4$
Di- α-(D,L)-alanylbacterioisochlorin $e_4$
Di- β-alanylbacterioisochlorin $e_4$
Di-ε-amino-n-caproylbacterioisochlorin $e_4$
Di, tri- (D,L)-serinylbacteriochlorin $e_6$
Di, tri- glycylbacteriochlorin $e_6$
Di, tri-α-(D,L)-alanylbacteriochlorin $e_6$
Di, tri- β-alanylbacteriochlorin $e_6$
Di, tri-ε-amino-n-caproylbacteriochlorin $e_6$ Similarly, by utilizing other amino acids, peptides which further illustrate embodiments of, but do not limit the present invention, can be employed:
Di-Threoninyl trans-mesochlorin IX
Di,tri-Threoninyl chlorin $e_6$
Di,tri-Threoninyl mesochlorin $e_6$
Di-Threoninyl chlorin $e_4$
Di-Threoninyl mesochlorin $e_4$
Di-Threoninyl isochlorin $e_4$
Di-Threoninyl mesoisochlorin $e_4$
Di-Threoninyl photoprotoporphyrin IX
Di-Threoninyl mesoporphyrin IX
Di-Threoninyl protoporphyrin IX
Di-Threoninyl deuteroporphyrin IX
Di,tri,tetra-Threoninyl coproporphyrin III
Di-Threoninyl hematoporphyrin IX
Di-Threoninyl bacteriochlorin $e_4$
Di-Threoninyl bacterioisochlorin $e_4$
Di,tri-Threoninyl bacteriochlorin $e_6$
Di-Cysteinyl trans-mesochlorin IX
Di,tri-Cysteinyl chlorin $e_6$
Di,tri-Cysteinyl mesochlorin $e_6$
Di-Cysteinyl chlorin $e_4$
Di-Cysteinyl isochlorin $e_4$
Di-Cysteinyl mesoisochlorin $e_4$
Di-Cysteinyl photoprotoporphyrin IX
Di-Cysteinyl mesoporphyrin IX
Di-Cysteinyl protoporphyrin IX
Di-Cysteinyl deuteroporphyrin IX
Di,tri,tetra-Cysteinyl-coproporphyrin III
Di-Cysteinyl hematoporphyrin IX
Di-Cysteinyl bacteriochlorin $e_4$
Di-Cysteinyl bacterioisochlorin $e_4$
Di,tri-Cysteinyl bacteriochlorin $e_6$
Di-Tyrosyl trans-mesochlorin IX
Di,tri-Tyrosyl chlorin $e_6$
Di,tri-Tyrosyl mesochlorin $e_6$
Di-Tyrosyl chlorin $e_4$
Di-Tyrosyl mesochlorin $e_4$
Di-Tyrosyl isochlorin $e_4$
Di-Tyrosyl mesoisochlorin $e_4$
Di-Tyrosyl photoprotoporphryin IX
Di-Tyrosyl mesoporphyrin IX
Di-Tyrosyl protoporphyrin IX
Di-Tyrosyl deuteroporphyrin IX
Di,tri,tetra-Tyrosyl coproporphyrin III
Di-Tyrosyl hematoporphryin IX
Di-Tyrosyl bacteriochlorin $e_4$
Di-Tyrosyl bacterioisochlorin $e_4$
Di,tri-Tyrosyl bacteriochlorin $e_6$
Di-Valyl trans-mesochlorin IX
Di,tri-Valyl chlorin $e_6$
Di,tri-Valyl mesochlorin $e_6$
Di-Valyl chlorin $e_4$
Di-Valyl mesochlorin $e_4$
Di-Valyl isochlorin $e_4$
Di-Valyl mesoisochlorin $e_4$
Di-Valyl photoprotoporphyrin IX
Di-Valyl mesoporphyrin IX
Di-Valyl protoporphyrin IX
Di-Valyl deuteroporphyrin IX
Di,tri,tetra-Valyl coproporphyrin III
Di-Valyl hematoporphyrin IX
Di-Valyl bacteriochlorin $e_4$
Di-Valyl bacterioisochlorin $e_4$
Di,tri-Valyl bacteriochlorin $e_6$
Di-Luccyl trans-mesochlorin IX
Di,tri-Leucyl chlorin $e_6$
Di,tri-Leucyl mesochlorin $e_6$
Di-Leucyl chlorin $e_4$
Di-Leucyl mesochlorin $e_4$
Di-Leucyl isochlorin $e_4$
Di-Leucyl mesoisochlorin $e_4$
Di-Leucyl photoprotoporphyrin IX
Di-Leucyl mesoporphyrin IX
Di-Leucyl protoporphyrin IX
Di-Leucyl deuteroporphyrin IX
Di,tri,tetra-Leucyl coproporphyrin III
Di-Leucyl hematoporphyrin IX
Di-Leucyl bacteriochlorin $e_4$
Di-Leucyl bacterioisochlorin $e_4$
Di,tri-Leucyl bacteriochlorin $e_6$
Di-Isoleucyl trans-mesochlorin IX
Di,tri-Isoleucyl chlorin $e_6$
Di,tri-Isoleucyl mesochlorin $e_6$
Di-Isoleucyl chlorin $e_4$
Di-Isoleucyl mesochlorin $e_4$
Di-Isoleucyl isochlorin $e_4$
Di-Isoleucyl mesoisochlorin $e_4$
Di-Isoleucyl photoprotoporphyrin IX
Di-Isoleucyl mesoporphyrin IX
Di-Isoleucyl protoporphyrin IX
Di-Isoleucyl deuteroporphyrin IX
Di,tri,tetra-Isoleucyl coproporphyrin III
Di-Isoleucyl hematoporphyrin IX Di-Isoleucyl bacteriochlorin e₄
Di-Isoleucyl bacterioisochlorin e₄
Di,tri-Isoleucyl bacteriochlorin e₆
Di-Prolyl trans-mesochlorin IX
Di,tri-Prolyl chlorin e₆
Di,tri-Prolyl mesochlorin e₆
Di-Prolyl chlorin e₄
Di-Prolyl mesochlorin e₄
Di-Prolyl isochlorin e₄
Di-Prolyl mesoisochlorin e₄
Di-Prolyl photoprotoporphyrin IX
Di-Prolyl mesoporphryin IX
Di-Prolyl protoporphyrin IX
Di-Prolyl deuteroporphyrin IX
Di,tri,tetra-Prolyl coproporphyrin III
Di-Prolyl hematoporphyrin IX
Di-Prolyl bacteriochlorin e₄
Di-Prolyl bacterisochlorin e₄
Di,tri-Prolyl bacteriochlorin e₆
Di-Phenylalanyl trans-mesochlorin IX
Di,tri-Phenylalanyl chlorin e₆
Di,tri-Phenylalanyl mesochlorin e₆
Di-Phenylalanyl chlorin e₄
Di-Phenylalanyl mesochlorin e₄
Di-Phenylalanyl isochlorin e₄
Di-Phenylalanyl mesoisochlorin e₄
Di-Phenylalanyl photoprotoporphyrin IX
Di-Phenylalanyl mesoporphyrin IX
Di-Phenylalanyl protoporphyrin IX
Di-Phenylalanyl deuteroporphyrin IX
Di,tri,tetra-Phenylalanyl coproporphyrin III
Di-Phenylalanyl hematoporphyrin IX
Di-Phenylalanyl bacteriochlorin e₄
Di-Phenylalanyl bacterioisochlorin e₄
Di,tri-Phenylalanyl bacteriochlorin e₆
Di-Tryptophyl trans-mesochlorin IX
Di,tri-Tryptophyl chlorin e₆
Di,tri-Tryptophyl mesochlorin e₆
Di-Tryptophyl chlorin e₄
Di-Tryptophyl mesochlorin e₄
Di-Tryptophyl isochlorin e₄
Di-Tryptophyl mesoisochlorin e₄
Di-Tryptophyl photoprotoporphyrin IX
Di-Tryptophyl mesoporphyrin IX
Di-Tryptophyl protoporphyrin IX
Di-Tryptophyl deuteroporphyrin IX
Di,tri,tetra-Tryptophyl coproporphyrin III
Di-Tryptophyl hematoporphyrin IX
Di-Tryptophyl bacteriochlorin e₄
Di-Tryptophyl bacterioisochlorin e₄
Di,tri-Tryptophyl bacteriochlorin e₆
Di-Methionyl trans-mesochlorin IX
Di,tri-Methionyl chlorin e₆
Di,tri-Methionyl mesochlorin e₆
Di-Methionyl chlorin e₄
Di-Methionyl mesochlorin e₄
Di-Methionyl isochlorin e₄
Di-Methionyl mesoisochlorin e₄
Di-Methionyl photoprotoporphyrin IX
Di-Methionyl mesoporphyrin IX
Di-Methionyl protoporphyrin IX
Di-Methionyl deuteroporphyrin IX
Di,tri,tetra-Methionyl coproporphyrin III
Di-Methionyl hematoporphryin IX
Di-Methionyl bacteriochlorin e₄
Di-Methionyl bacterioisochlorin e₄
Di,tri-Methionyl bacteriochlorin e₆
Di-Histidyl trans-mesochlorin IX
Di,tri-Histidyl Chlorin e₆
Di,tri-Histidyl mesochlorin e₆
Di-Histidyl chlorin e₄
Di-Histidyl mesochlorin e₄
Di-Histidyl isochlorin e₄
Di-Histidyl mesoisochlorin e₄
Di-Histidyl photoprotoporphyrin IX
Di-Histidyl mesoporphyrin IX
Di-Histidyl protoporphyrin IX
Di-Histidyl deuteroporphyrin IX
Di,tri,tetra-Histidyl coproporphyrin III
Di-Histidyl hematoporphyrin IX
Di-Histidyl bacteriochlorin e₄
Di-Histidyl bacterioisochlorin e₄
Di,tri-Histidyl bacteriochlorin e₆
Di-Arginyl trans-mesochlorin IX
Di,tri-Arginyl chlorin e₆
Di,tri-Arginyl mesochlorin e₆
Di-Arginyl chlorin e₄
Di-Arginyl mesochlorin e₄
Di-Arginyl isochlorin e₄
Di-Arginyl mesoisochlorin e₄
Di-Arginyl photoprotoporphyrin IX
Di-Arginyl mesoporphryin IX
Di-Arginyl protoporphyrin IX
Di-Arginyl deuteroporphyrin IX
Di,tri,tetra-Arginyl coproporphyrin III
Di-Arginyl hematoporphyrin IX
Di-Arginyl bacteriochlorin e₄
Di-Arginyl bacterioisochlorin e₄
Di,tri-Arginyl bacteriochlorin e₆
Di-Lysyl trans-mesochlorin IX
Di,tri-Lysyl chlorin e₆
Di,tri-Lysyl mesochlorin e₆
Di-Lysyl chlorin e₄
Di-Lysyl mesochlorin e₄
Di-Lysyl isochlorin e₄
Di-Lysyl mesoisochlorin e₄
Di-Lysyl photoprotoporphyrin IX
Di-Lysyl mesoporphyrin IX
Di-Lysyl protoporphyrin IX
Di-Lysyl deuteroporphyrin IX
Di,tri-tetra-Lysyl coproporphyrin III
Di-Lysyl hematoporphyrin IX
Di-Lysyl bacteriochlorin e₄
Di-Lysyl bacterioisochlorin e₄
Di,tri-Lysyl bacteriochlorin e₆
Di-Glutaminyl trans-mesochlorin IX
Di,tri-Glutaminyl chlorin e₆
Di,tri-Glutaminyl mesochlorin e₆
Di-Glutaminyl chlorin e₄
Di-Glutaminyl mesochlorin e₄
Di-Glutaminyl isochlorin e₄
Di-Glutaminyl mesoisochlorin e₄
Di-Glutaminyl photoprotoporphyrin IX
Di-Glutaminyl mesoporphyrin IX
Di-Glutaminyl protoporphyrin IX
Di-Glutaminyl deuteroporphyrin IX Di,tri,tetra-Glutaminyl coproporphyrin III
Di-Glutaminyl hematoporphyrin IX
Di-Glutaminyl bacteriochlorin $e_4$
Di-Glutaminyl bacterioisochlorin $e_4$
Di,tri-Glutaminyl bacteriochlorin $e_6$
Di-Asparginyl trans-mesochlorin IX
Di,tri-Asparginyl chlorin $e_6$
Di,tri-Asparginyl mesochlorin $e_6$
Di-Asparginyl chlorin $e_4$
Di-Asparginyl mesochlorin $e_4$
Di-Asparginyl isochlorin $e_4$
Di-Asparginyl mesoisochlorin $e_4$
Di-Asparginyl photoprotoporphyrin IX
Di-Asparginyl mesoporphyrin IX
Di-Asparginyl protoporphyrin IX
Di-Asparginyl deuteroporphyrin IX
Di,tri,tetra-Asparginyl coproporphyrin III
Di-Asparginyl hematoporphyrin IX
Di-Asparginyl bacteriochlorin $e_4$
Di-Asparginyl bacterioisochlorin $e_4$
Di,tri-Asparginyl bacteriochlorin $e_6$ Monoamides

EXAMPLE 8

Mono (DL) serinyl mesoporphyrin IX (mixed anhydride method)

400 mg (0.0007 moles) of mesoporphyrin IX was suspended in 50 ml of tetrahydrofuran (THF). 360 μl (0.0035 moles) of triethylamine was added with stirring. After 10 minutes, 340 μl (0.0031 moles) ethyl chloroformate was added. After stirring 10 minutes, 10 ml (0.01 moles) of 1M KOH containing 761 mg (0.0072 moles) of DL serine was added to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatrogram.

After checking for product, the solution was adjusted to pH 7.5–8.0 and placed on a reverse phase (C-18 silica) column 2.5×30 cm. The reaction mixture resolved using a linear gradient of 20–70% methanol was in 0.01M KPO$_4$ buffer pH 6.85 (1 liter total volume).

The column effluent was collected via fraction collector and the tube contents were pooled according to individual components. The order of elution was diserinyl mesoporphyrin IX, monoserinyl mesoporphyrin IX and unsubstituted mesoporphyrin IX.

The methanol was flashed off and the material was precipitated at pH 2.5–3.0. The ppt. was washed 3 times with dilute acetic acid in water. The product was dried under vacuum.

EXAMPLE 9

Mono qlycyl mesoporphyrin IX (mixed anhydride method)

100 mg (0.000175 moles) of mesoporphyrin IX was suspended in 100 ml of tetrahydrofuran (THF). 360 μl (0.0035 moles) of triethylamine was added with stirring. After 10 minutes, 340 μl (0.0031 moles) of ethylchloroformate was added. After stirring 10 minutes, 10 ml (0.01 moles) of 1M KOH containing 500 mg (0.0066 moles) of glycine was added to the THF solution. This mixture was stirred 60 minutes at room temperature.

The organic solvent was flashed off and the reaction mixture was checked by silica TLC for product. Benzene/methanol/88% formic acid (8.5/1.5/0/13) was used to develop the chromatogram.

After checking for product, the solution was adjusted to pH 7.5–8.0 and placed on a reverse phase (C-18 silica) column 2.5×30 cm. The reaction mixture was resolved using a linear gradient of zero to 50% methanol in 0.01M KPO$_4$ buffer pH 6.85 (1 l total volume).

The column effluent was collected in a fraction collector and the contents were sorted according to individual components. The order of elution was diglycyl mesoporphyrin IX, monoglycyl mesoporphyrin IX and unsubstituted mesoporphyrin IX.

The methanol was flashed off and the material was precipitated at pH 2.5–3.0. The ppt. was washed 3 times with dilute acetic acid in water. The product was dried under vacuum.

EXAMPLE 10

Mono α(DL) alanyl mesoporphyrin IX (Mixed anhydride method)

100 mg (0.000175 moles) of mesoporphyrin IX was suspended in 100 ml of tetrahydrofuran (THF). 210 μl (0.002 moles) of triethylamine was added with stirring. After 10 minutes 195 μl (0.00177 moles) of ethylchloroformate was added. After stirring 10 minutes, 10 ml (0.01 moles) of 1M KOH containing 500 mg (0.0056 moles) of α(DL) alanine was added to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatogram.

After checking for product, the solution was adjusted to pH 7.5–8.0 and placed on a reverse phase (C-18 silica) column 2.5×30 cm. The reaction mixture was resolved using a linear gradient of 20–70% methanol in 0.01M KPO$_4$ buffer pH 6.85 (1 l total volume).

The column effluent was collected via fraction collection and the tube contents were sorted according to individual components. The order of elution was di-α(DL) alanyl mesoporphyrin IX, mono- α(DL)-alanyl mesoporphyrin IX and unsubstituted mesoporphyrin IX.

The methanol was flashed off and the material was precipitated at pH 2.5–3.0. The ppt. was washed 3 times with dilute acetic acid in water. The product was dried under vacuum.

EXAMPLE 11

Mono β alanyl mesoporphyrin IX (mixed anhydride method)

400 mg (0.0007 moles) of mesoporphyrin IX was suspended in 100 ml of tetrahydrofuran (THF). 360 μl (0.0035 moles) of triethylamine was added with stirring. After 10 minutes, 340 μl (0.0031 moles) ethyl chloroformate was added. After stirring 10 minutes, 10 ml (0.01 moles) of 1M KOH containing 400 mg (0.0044 moles) of βalanine was added to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatogram.

After checking for product, the solution was adjusted to pH 7.5–8.0 and placed on a reverse phase (C-18 silica) column 2.5×30 cm. The reaction mixture was resolved using a linear gradient of 40-80% methanol in 0.01 M KPO$_4$ buffer pH 6.85 (1 l total volume).

The column effluent was collected via fraction collector and the tube contents were pooled according to individual components. The order of elution was di-$\beta$-alanyl mesoporphyrin IX, mono-$\beta$-alanyl mesoporphyrin IX, and unsubstituted mesoporphyrin IX.

The methanol was flashed off and the material was precipitated at pH 2.5-3.0. The ppt. was washed 3 times with dilute acetic acid in water. The product was dried under vacuum. The yield for mono-$\beta$-alanyl mesoporphyrin IX was 23 mg.

EXAMPLE 12

Mono $\epsilon$ amino-n-caproyl mesoporphyrin IX (mixed anhydride method)

400 $\mu$g (0.0007 moles) of mesoporphyrin IX was suspended in 50 ml of tetrahydrofuran (THF). 360 $\mu$l (0.0035 moles) of triethylamine was added with stirring. After 10 minutes, 340 $\mu$l (0.00414 moles) of ethylchloroformate was added. After stirring 10 minutes, 10 ml (0.01 moles) of 1M KOH containing 543 mg (0.00369 moles) of $\epsilon$-amino-n-caproic acid was added to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatogram.

After checking for product, the solution was adjusted to pH 7.5-8.0 and placed on a reverse phase (C-18 silica) column 2.5×30 cm. The reaction mixture was resolved using a linear gradient of 20-70% methanol in 0.01M KPO$_4$ buffer pH 6.85 (1 l total volume).

The column effluent was collected via fraction collector and the tube contents were pooled according to individual components. The order of elution was di-$\epsilon$-amino-n-caproyl mesoporphyrin IX, mono-$\epsilon$-amino-n-caproyl mesoporphyrin IX, and unsubstituted mesoporphyrin IX.

The methanol was flashed off and the material was precipitated at pH 2.5-3.0. The ppt. was washed three times with dilute acetic acid in water. The product was dried under vacuum.

EXAMPLE 13

Mono-$\beta$-alanyl Hematoporphyrin IX (mixed anhydride method)

400 mg (0.00059 moles) Hematoporphyrin IX dihydrochloride was suspended in 50 ml of tetrahydrofuran (THF).

36 $\mu$l (0.0035 moles) of triethylamine was added with stirring. After 10 minutes, 340 $\mu$l (0.0031 moles) of ethyl chloroformate was added. After stirring 10 minutes, 10 ml (0.01 moles) of 1M KOH containing 400 mg (0.0044 moles) of $\beta$-alanine was added to the THF solution. This mixture was stirred 60 minutes at room temperature.

The organic solvent was removed by flash evaporation, keeping the temperature below 50° C. The reaction mixture was checked for product by silica TLC using Benzene/methanol 88% formic acid (8.5/1.5/0.13) as solvent to develop the chromatogram.

The solution was adjusted to pH 7.5-8.0 with HCl and placed on reverse phase (C-18 silica) column 2.5×30 cm. The mixture was resolved using a linear gradient of 40-80% methanol in 0.01M KPO$_4$ buffer pH 6.85 (1 liter total volume). The individual components were collected as they came off the column in the order di-$\beta$-alanyl hematoporphyrin IX, mono-$\beta$-alanyl hematoporphyrin IX and hematoporphyrin IX.

The methanol was removed from each component by flash evaporation and the material was precipitated by adjusting the pH to 2.5 -3.0 using HCl. The precipitate was washed three times with dilute acetic acid in water at the centrifuge and the products dried under vacuum. The yield of di-$\beta$-alanyl hematoporphyrin IX was 52mg and of mono-$\beta$-alanyl hematoporphyrin was 30 mg.

EXAMPLE 14

Mono Glycyl Chlorin e$_6$ (Mixed Anhydride Method)

625 mg of chlorin e$_6$ was dissolved in 300 ml of dimethyl formamide (DMF) and 277 $\mu$l (0.002 moles) of triethylamine (TEA) was added to the DMF solution. After stirring for five minutes, 201 $\mu$l (0.002 moles) of ethylchloroformate (EC) was added and stirred for 1½ hours at room temperature.

75 mg (0.0009 moles) of glycine (ammonia free) was added to the DMF solution and allowed to stir three hours at 50°-60° C.

The DMF solution was tested for product by reverse phase (C-18 silica) TLC using methanol/0.01M sodium phosphate buffer, pH 6.85, 70/30, to develop the chromatogram.

The DMF solution was flashed to near dryness, then dissolved in dilute NaOH and the pH adjusted to 2.5-3 to precipitate the solid. The precipitate was then placed on a reverse phase (C-18 silica) column 3.7 cm×45 cm.

Fractions were eluted, using 20-40% methanol in 0.01M sodium phosphate buffer, pH 6.85. The fractions were pooled according to individual components.

The methanol was flashed off and the material was precipitated at pH 2.5-3.0. The precipitate was washed and centrifuged 3 times in dilute acetic acid in water. The product was dried under vacuum. The yield of mono glycyl chlorin e$_6$ was 87.5 mg.

Utilizing the aforementioned carbodiimide or the mixed anhydride methods of Examples 8-14, the following preferred monoamide compounds of this invention are synthesized:

Chlorin Derivatives (DL)-Serinyl-trans-mesochlorin IX
Glycyl-trans-mesochlorin IX
$\alpha$-(DL)-Alanyl-trans-mesochlorin IX
$\beta$-Alanyl-trans-mesochlorin IX
$\epsilon$-Amino-n-caproyl-mesochlorin IX
(D,L)-Serinyl chlorin e$_6$
(D,L)-Serinyl mesochlorin e$_6$
Glycyl chlorin e$_6$
Glycyl mesochlorin e$_6$
$\alpha$-(D,L)-Alanyl chlorin e$_6$
$\alpha$-(D,L) Alanyl mesochlorin e$_6$
$\beta$-Alanyl chlorin e$_6$
$\beta$-Alanyl mesochlorin e$_6$
$\epsilon$-Amino-n-caproyl chlorin e$_6$
$\epsilon$-Amino-n-caproyl mesochlorin e$_6$
(D,L)-Serinyl chlorin e$_4$
(D,L)-Serinyl mesochlorin e$_4$
(D,L)-Serinyl isochlorin e$_4$
(D,L)-Serinyl mesoisochlorin e$_4$
Glycyl chlorin e$_4$ Glycyl mesochlorin $e_4$
Glycyl isochlorin $e_4$
Glycyl mesoisochlorin $e_4$
α-(DL)-Alanyl chlorin $e_4$
α-(DL)-Alanyl mesochlorin $e_4$
α-(DL)-Alanyl isochlorin $e_4$
α-(DL)-Alanyl mesoisochlorin $e_4$
β-Alanyl chlorin $e_4$
β-Alanyl mesochlorin $e_4$
β-Alanyl isochlorin $e_4$
β-Alanyl mesoisochlorin $e_4$
ε-Amino-n-caproyl chlorin $e_4$
ε-Amino-n-caproyl mesochlorin $e_4$
ε-Amino-n-caproyl isochlorin $e_4$
ε-Amino-n-caproyl mesoisochlorin $e_4$
(D,L)-Serinyl pyropheophorbide a
Glycyl pyropheophorbide a
α-(D,L)-Alanyl pyropheophorbide a
β-Alanyl pyropheophorbide a
ε-Amino-n-caproyl pyropheophorbide a
(D,L)-Serinylpheophorbide a
Glycyl pheophorbide a
α-(D,L)-Alanylpheophorbide a
β-Alanylpheophorbide a
ε-Amino-n-caproylpheophorbide a
(D,L)-Serinylphotoprotoporphyrin IX
Glycylphotoprotoporphyrin IX
α-(D,L)-Alanylphotoprotoporphyrin IX
β-Alanylphotoprotoporphyrin IX
ε-Amino-n-caproylphotoprotoporphyrin IX Porphyrin Derivatives (D,L)-Serinylmesoporphyrin IX
Glycylmesoporphyrin IX
α-(DL)-Alanylmesoporphyrin IX
β-Alanylmesoporphyrin IX
ε-Amino-n-caproylmesoporphyrin IX
(D,L)-Serinylprotoporphyrin IX
Glycylprotoporphyrin IX
α-(D,L)-Alanylprotoporphyrin IX
β-Alanylprotoporphyrin IX
ε-Amino-n-caproylprotoporphyrin IX
(D,L)-Serinyldeuteroporphyrin IX
Glycyldeuteroporphyrin IX
α-(D,L)-Alanyldeuteroporphyrin IX
β-Alanyldeuteroporphyrin IX
ε-Amino-n-caproyldeuteroporphyrin IX
tetra- (D,L)-Serinylcoproporphyrin III
tetra- Glycylcoproporphyrin III
tetra-α-(D,L)- Alanylcoproporphyrin III
tetra-β-Alanylcoproporphyrin III
tetra-ε-Amino-n-caproylcoproporphyrin III
(D,L)-Serinylhematoporphyrin IX
Glycylhematoporphyrin IX
α-(D,L)-Alanylhematoporphyrin IX
β-Alanylhematoporphyrin IX
ε-Amino-n-caproylhematoporphyrin IX Bacteriochlorin Derivatives (D,L)-Serinylbacteriochlorin $e_4$
Glycylbacteriochlorin $e_4$
α-(DL)-Alanylbacteriochlorin $e_4$
β-Alanylbacteriochlorin $e_4$
ε-Amino-n-caproylbacteriochlorin $e_4$
(D,L)-Serinylbacterioisochlorin $e_4$
Glycylbacterioisochlorin $e_4$
α-(DL)-Alanylbacterioisochlorin $e_4$
β-Alanylbacterioisochlorin $e_4$
ε-Amino-n-caproylbacterioisochlorin $e_4$
(D,L)-Serinylbacteriochlorin $e_6$
Glycylbacteriochlorin $e_6$
α-(DL)-Alanylbacteriochlorin $e_6$
β-Alanylbacteriochlorin $e_6$
ε-Amino-n-caproylbacteriochlorin $e_6$
(D,L)-Serinylpyrobacteriopheophorbide a
Glycylpyrobacteriopheophorbide a
α-(D,L) Alanylpyrobacteriopheophorbide a
β-Alanylpyrobacteriopheophorbide a
ε-Amino-n-caproylpyrobacteriopheophorbide a
(D,L)-Serinylbacteriopheophorbide a
Glycylbacteriopheophorbide a
α-(D,L)-Alanylbacteriopheophorbide a
β-Alanylbacteriopheophorbide a
ε-Amino-n-caproylbacteriopheophorbide a Other amino acid derivatives of the tetrapyrroles can also be prepared. The following amino acids can also be used to prepare the mono- di-, tri-, or where appropriate, the tetra-amino acid derivatives of the chlorins, porphyrins, or bacteriochlorins, employing the procedures of one of the aforementioned methods: Piperidine-2-carboxylic acid, Piperidine-6-carboxylic acid, Pyrrole-2-carboxylic acid, Pyrrole-5-carboxylic acid, Piperidine-6-propionic acid, and Pyrrole-5-acetic acid Mixed amino acid derivatives of the tetrapyrroles can also be prepared. The various chlorin derivatives, porphyrin derivatives and bacteriochlorin derivatives can include any two or three of the following amino acids: Glycine, Serine, Threonine, Cysteine, Tyrosine, Asparagine, Glutamine, Lysine, Arginine, Histidine, α-Alanine, β-Alanine, Valine, Leucine, Isoleucine, Proline, α-Phenylalanine, β-Phenylalanine, Tryptophan, Methionine, ε-Amino-n-caproic acid, Piperidine-2-carboxylic acid, Pyrrole-5-carboxylic acid, Piperidine-6-propionic acid, Pyrrole-5-acetic acid.

Physical characteristics of the compounds (relative polarity) is measured by a standard chromatographic system. The chromatographic data (Rf values) were measured on Baker silica gel-C18 thin layer chromatographic plates, the particle size of which is 20 μM, and the coating thickness of which is 200 μM. The solvent system for these chromatographic runs consisted of 75% methanol, and 25% 0.01 M potassium phosphate buffer, pH 6.85. The Rf values for the various derivatives are tabulated in TABLE 1. Spectroscopic data are indicated in TABLE 2.

TABLE 1

| Rf VALUES | | |
|---|---|---|
| Compounds | Derivative | Rf |
| Mesoporphyrin IX | — | .32 |
| Mesoporphyrin IX | mono-α-alanyl | .44 |
| Mesoporphyrin IX | mono-β-alanyl | .44 |
| Mesoporphyrin IX | di-α-alanyl | .51 |
| Mesoporphyrin IX | di-β-alanyl | .49 |
| Mesoporphyrin IX | mono-glycycl | .47 |
| Mesoporphyrin IX | di-seryl | .58 |
| Mesoporphyrin IX | di-glycyl | .54 |
| Mesoporphyrin IX | di-ε-aminocaproyl | .34 |
| Hematoporphyrin IX | — | .78 |
| Hematoporphyrin IX | mono-β-alanyl | .83 |
| Hematoporphyrin IX | di-β-alanyl | .83 |
| Chlorin $e_6$ | — | .66 |
| Chlorin $e_6$ | di-L-α-serinyl | .78 |

TABLE II

Spectroscopic Absorption Data

| Compounds | Absorption Maxima (nm) in Visible Region | mM Extinction Coefficient (EmM) ± 10% | Soret Band nM |
|---|---|---|---|
| Photoprotoporphyrin IX isomer mixture | 668 | 38 | 415 |
| Pheophorbide a | 667 | 35 | 408.6 |
| Pyropheophorbide a | 668 | 38 | 411.2 |
| Trans-mesochlorin IX | 643 | 60 | 388 |
| Chlorin $e_6$ | 665.6 | 42 | 402 |
| Bacteriopheophorbide a | 753.5 | 44.7 | 359 |
| Hematoporphyrin derivative (HPD) | 626 | 2.9 | 399 |

Solvent in all cases is p-dioxane.

The following protocol describes the procedure for the utilization of these new compounds of the present invention in the treatment of rat tumors.

PROCEDURE

The photodynamic therapy experiments have been carried out on Buffalo rats, using the transplantable tumor, Morris Hepatoma 7777. The tumors were transplanted subcutaneously on the outside of the thigh. During treatment, the tumors ranges in size between 1 and 2.5 cm in diameter.

The general treatment regime is as follows. The rats are injected with a solution of the chlorin prepared as follows: 20 mg of the sodium salt of the chlorin was dissolved in 1 ml of 0.9% NaCl. The chlorin solution was then injected intravenously through the external jugular while the rat was anesthetized with ether. The volume of solution injected was calculated based upon the weight of the animal and the dosage, on a weight to weight basis, for the particular experiment. A specified time interval was then allowed to elapse before light treatment was instigated.

Light treatment of the rats was without anesthesia. The rats were restrained, the hair removed in the treatment area and treated with laser light from a Cooper Aurora argon pumped, tunable dye laser.

The laser was equipped with a fiber optic light delivery system coupled to a microlens system developed by Dr. Daniel Doiron, D.R.D. Consulting, Santa Barbara, Calif.

The lens disperses the laser beam, providing a circular distribution of light with homogeneous light intensity throughout the area of the incident light beam. The wavelength of light was adjusted using a Hartridge reversion spectroscope. The light intensity was determined using a Yellow Springs Instrument, Model 65A, radiometer.

The micro lens was positioned at such a distance from the skin of the animal so as to provide an illumination diameter of 1.5cm, and the light flux was varied by control of the laser output.

Subsequent to illumination, the animal was returned to its cage and, 24 hours later, it was treated intravenously in the external jugular vein with 14 mg of Evans Blue dye, dissolved in 250 μl of 0.9% NaCl. Two hours after injection, the rat was sacrificed and the tumor cross-sectioned. The extent of tumor necrosis was assessed by the lack of dye uptake ([1]), and the depth of the necrotic cross section of the tumor was recorded in millimeters.

(1) M. C. Berenbaum, Br. J. Cancer 45: 571(1982)

Table III summarizes the effects of these drugs on tumors and includes a range of wavelengths, dosages, intensities, and time intervals for treatment. This has been necessary, in order to attempt to establish the optimal conditions for phototherapy utilizing this new drug. The conditions described result in measurable and significant damage to the tumors.

In all cases except where noted, tissue damage occurred selectively to the tumor tissue as assayed by the Evans Blue method, even though, in nearly all cases, normal skin overlayed the tumor and the treatment area overlapped significant areas of normal muscle tissue.

The photodynamic therapy date is presented in tabular form. Column No. 2 is the total light dose administered in terms of Joules per square centimeter. Column No. 3 is the dose of chlorin administered in terms of mg of drug per kilogram of rat body weight. Column No. 4 is the time lapse between administration of drug and treatment with laser light. Column No. 5 is the wavelength of treatment light in nanometers. Column No. 6 is the intensity of the treatment light in milliwatts per square centimeter. In Column No. 7, $\bar{x}$ is the mean depth of necrosis in millimeters of the tumor tissue, i.e., the distance from the necrotic top of the tumor next to the skin to the necrotic edge of the tumor most distant from the skin.

S.D. is the standard deviation of $\bar{x}$.

(N) is the number of tumors or legs involved in the experiment.

Column No. 8 is the range of depth of necrosis in millimeters within the group.

TABLE III

| Tumor | Joules/ $cm^2$ | Drug dose mg/kg | Time in hrs btwn drugs & light | Wave lnth nm | Intensity $mW/cm^2$ | Range $\bar{x}$ s.d. | (n) | mm |
|---|---|---|---|---|---|---|---|---|
| Mono Glycyl chlorin $e_6$ | | | | | | | | |
| 7777 | 20 | 20 | 24 | 665 | 100 | 3.9 ± 3.0 | (5) | 2–9* |
| Mono-L-α-alanyl chlorin $e_6$ | | | | | | | | |
| 7777 | 20 | 20 | 24 | 665 | 100 | 3.8 ± 1.8 | (2) | 2.5–5 |
| Mono-L-α-serinyl chlorin $e_6$ | | | | | | | | |
| 7777 | 20 | 20 | 24 | 665 | 100 | 6.3 ± 2.7 | (6) | 3–10 |
| Diglycyl chlorin $e_6$ | | | | | | | | |
| 7777 | 20 | 20 | 24 | 665 | 100 | 4.7 ± 1.0 | (3) | 3.5–5.5 |

*3 of 8 tumors showed no necrosis due to drug and light.

What is claimed is:

1. A therapeutic composition for the detection and treatment of tumors sensitive thereto comprising a therapeutically effective amount of a fluorescent mono, di or polyamide of a aminomonocarboxylic acid and a tetrapyrrole compound of the formula:

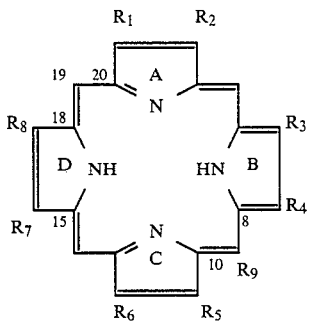

or the corresponding di- or tetrahydrotetrapyrroles wherein $R_1$ is methyl;

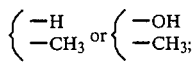

$R_2$ is H, vinyl, ethyl,

acetyl,

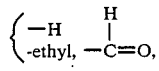

$CH_2CH_2CO_2H$, or $=CHCHO$;

$R_3$ is methyl

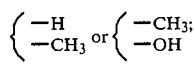

$R_4$ is H, vinyl, ethyl,

$CH_2CH_2CO_2H$, $=CHCHO$; or

$R_5$ is methyl;
$R_6$ is H, $CH_2CH_2CO_2H$, $CH_2CH_2CO_2R$ or $CO_2H$;
$R_7$ is $CH_2CH_2CO_2H$, $CH_2CH_2CO_2R$, or

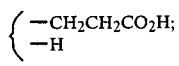

$R_8$ is methyl or

$R_9$ is H, COOH, $CH_2COOH$ or methyl;

provided that when $R_1$, $R_2$, $R_3$, $R_4$, $R_7$ and $R_8$ represent two substituents or are divalent and attached to the same carbon, the respective pyrrole ring to which attached is a dihydropyrrole;

R is lower alkyl or benzyl;

$R_6$ and $R_9$, taken together are

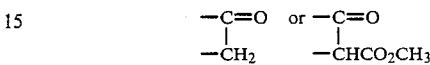

with the proviso that at least one of $R_1$–$R_9$ includes a free carboxyl group, or salts thereof; and a pharmaceutically acceptable carrier therefor.

2. The composition according to claim 1 wherein the tetrapyrrole is a porphyrin.

3. Composition according to claim 1 wherein the tetrapyrrole is a bacteriochlorin, di- or triamide.

4. Composition according to claim 1 wherein the amide-containing substituents are asymmetrically arranged on the tetrapyrrole molecule.

5. Composition according to claim 1 wherein the amide-containing substituents are asymmetrically arranged on the tetrapyrrole molecule.

6. Composition according to claim 1 wherein the amide is diserinyl mesoporphyrin IX.

7. Composition according to claim 1 wherein the amide is diglycyl mesoporphyrin IX.

8. Composition according to claim 1 wherein the amide is di-α-(DL)-alanyl mesoporphyrin IX.

9. Composition according to claim 1 wherein the amide is di-β-alanyl mesoporphyrin IX.

10. Composition according to claim 1 wherein the amide is di-ε-amino-n-caproyl mesoporphyrin IX.

11. Composition according to claim 1 wherein the amide is diglycyl trans-mesochlorin IX.

12. Composition according to claim 1 wherein the amide is diglycyl trans-mesochlorin $e_6$.

13. Composition according to claim 1 wherein the amide is diglycyl mesochlorin $e_4$.

14. Composition according to claim 1 wherein the amide is diglycyl hematoporphyrin IX.

15. Composition according to claim 1 wherein the amide is diglycyl chlorin $e_6$.

16. Composition according to claim 1 wherein the amide is diglycyl protoporphyrin IX.

17. Composition according to claim 1 wherein the amide is diglycyl deuteroporphyrin.

18. Composition according to claim 1 wherein the amide is di-α-(DL)-alanyl trans-mesochlorin IX.

19. Composition according to claim 1 wherein the amide is di-α-(DL)-alanyl mesochlorin $e_6$.

20. Composition according to claim 1 wherein the amide is di-α-(DL)-alanyl mesochlorin $e_4$.

21. Composition according to claim 1 wherein the amide is di-α-(DL)-alanyl hematoporphyrin IX.

22. Composition according to claim 1 wherein the amide is di-α-(DL)-alanyl chlorin $e_6$.

23. Composition according to claim 1 wherein the amide is di-α-(DL)-alanyl protoporphyrin IX.

24. Composition according to claim 1 wherein the amide di-α-(DL)-alanyl deuteroporphyrin. is 25. Composition according to claim 1 wherein the amide is di-β-DL)-alanyl trans-mesochlorin IX.

26. Composition according to claim 1 wherein the amide is di-β-DL)-alanyl mesochlorin $e_6$.

27. Composition according to claim 1 wherein the amide is di-β-(DL)-alanyl mesochlorin $e_4$.

28. Composition according to claim 1 wherein the amide is di-β-(DL)-alanyl hematoporphyrin IX.

29. Composition according to claim 1 wherein the amide is di-β-(DL)-chlorin $e_6$.

30. Composition according to claim 1 wherein the amide is di-β-(DL)-alanyl protoporphyrin IX.

31. Composition according to claim 1 wherein the amide is di-β-(DL)-alanyl deuteroporphyrin.

32. Composition according to claim 1 wherein the amide is di-L-α-serinyl chlorin $e_6$.

33. Composition according to claim 1 wherein the amide is di-L-α-serinyl trans-mesochlorin $e_6$.

34. Composition according to claim 1 wherein the amide is di-L-α-serinyl trans-mesochlorin IX.

35. Composition according to claim 1 wherein the amide is di-L-α-serinyl trans-mesochlorin $e_4$.

36. Composition according to claim 1 wherein the amide is di-L-α-serinyl hematoporphyrin IX.

37. Composition according to claim 1 wherein the amide is di-L-α-serinyl protoporphyrin IX.

38. Composition according to claim 1 wherein the amide is di-L-α-serinyl deuteroporphyrin.

39. Composition according to claim 1 wherein the amide is di-ε-amino-n-caproyl-hematoporphyrin IX.

40. Composition according to claim 1 wherein the amide is di-ε-amino-n-caproyl-chlorin $e_6$.

41. Composition according to claim 1 wherein the amide is di-ε-amino-n-caproyl-protoporphyrin IX.

42. Composition according to claim 1 wherein the amide is di-ε-amino-n-caproyl-deuteroporphyrin.

43. A method for detecting tumors sensitive thereto in a mammal comprising administering to said mammal a therapeutically effective amount of fluorescent mono, di or polyamide of an aminomonocarboxylic acid and a tetrapyrrole compound of the formula:

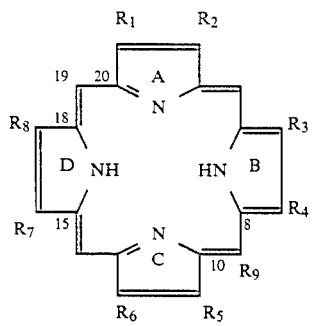

or the corresponding di- or tetrahydrotetrapyrroles wherein $R_1$ is methyl;

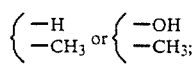

$R_2$ is H, vinyl, ethyl,

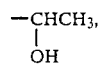

acetyl,

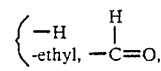

$CH_2CH_2CO_2H$, or $=CHCHO$;

$R_3$ is methyl

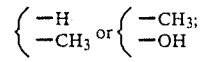

$R_4$ is H, vinyl, ethyl,

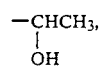

$CH_2CH_2CO_2H$, $=CHCHO$; or

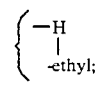

$R_5$ is methyl;

$R_6$ is H, $CH_2CH_2CO_2H$, $CH_2CH_2CO_2R$ or $CO_2H$;

$R_7$ is $CH_2CH_2CO_2H$, $CH_2CH_2CO_2R$, or

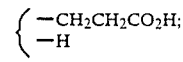

$R_8$ is methyl or

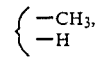

$R_9$ is H, COOH, $CH_2COOH$ or methyl; provided that when $R_1$, $R_2$, $R_3$, $R_4$, $R_7$ and $R_8$ represent two substituents or are divalent and attached to the same carbon, the respective pyrrole ring to which attached is a dihydropyrrole;

R is lower alkyl or benzyl;

$R_6$ and $R_9$, taken together are

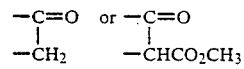

with the proviso that at least one of $R_1$–$R_9$ includes a free carboxyl group, or salts thereof; applying light of sufficient wavelength to activate said mono-, di- or polyamide to the area of the mammal to be examined; and observing the emitted fluorescence from said tumor.

44. A method for detecting tumors according to claim 43 wherein light from 360–760 nanometers is used for the diagnosis of the tumor.

45. A method for treating tumors sensitive thereto in a mammal comprising administering to said mammal a therapeutically effective amount of a fluorescent mono, di or polyamide of an aminomonocarboxylic acid and a tetrapyrrole compound of the formula:

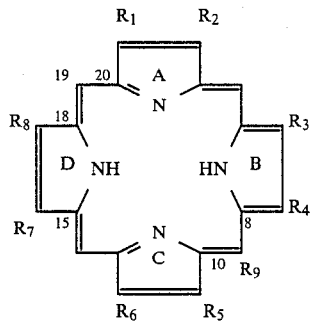

or the corresponding di- or tetrahydrotetrapyrroles wherein $R_1$ is methyl;

$$\begin{cases} -H \\ -CH_3 \end{cases} \text{or} \begin{cases} -OH \\ -CH_3; \end{cases}$$

$R_2$ is H, vinyl, ethyl,

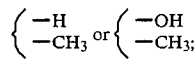

acetyl,

$CH_2CH_2CO_2H$, or $=CHCHO$;

$R_3$ is methyl,

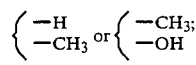

$R_4$ is H, vinyl, ethyl,

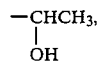

$CH_2CH_2CO_2H$, $=CHCHO$; or

$R_5$ is methyl;
$R_6$ is H, $CH_2CH_2CO_2H$, $CH_2CH_2CO_2R$ or $CO_2H$;
$R_7$ is $CH_2CH_2CO_2H$, $CH_2CH_2CO_2R$, or

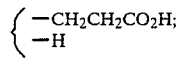

$R_8$ is methyl or

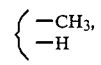

$R_9$ is H, COOH, $CH_2COOH$ or methyl; provided that when $R_1$, $R_2$, $R_3$, $R_4$, $R_7$ and $R_8$ represent two substituents or are divalent and attached to the same carbon, the respective pyrrole ring to which attached is a dihydropyrrole;
R is lower alkyl or benzyl;
$R_6$ and $R_9$, taken together are

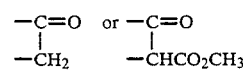

with the proviso that at least one of $R_1$–$R_9$ includes a free carboxyl group, or salts thereof; and applying light of sufficient wavelength and intensity to activate said mono-, di- or polyamide, whereby said mono-, di- or polyamide exerts a cell-killing effect on such tumor.

46. A method for treating tumors according to claim 45 whereby light from 620–760 nanometers is used for the treatment of the tumor.

* * * * *

UNITED STATES PATENT AND TRADEMARK OFFICE
CERTIFICATE OF CORRECTION

PATENT NO. : 4,977,177

DATED : December 11, 1990

INVENTOR(S) : Jerry C. Bommer, et al.

It is certified that error appears in the above-identified patent and that said Letters Patent is hereby corrected as shown below:

Column 1, line 24: "tumor.inhibiting" should read as --tumor inhibiting--

Column 9, line 10: "solc" should read as --sole--

Column 9, line 28: "applied For" should read as --applied. For--

Column 9, line 63: "one" should read as --one.--

Column 10, line 5: "salt The" should read as --salt. The--

Column 10, line 9: "highintensity" should read as --high-intensity--

Column 10, line 11: "limits power" should read as --limits: power--

Column 10, line 27: "Chlorophvll" should read as --Chlorophyll--

Column 10, line 39: "mesocchlorin" should read as --Mesocchlorin--

Column 10, line 63: "and." should read as --and--

Column 13, line 33: "(1 1 total" should read as --(1 ℓ total--

Column 13, line 64: "(1 1 total" should read as --(1 ℓ total--

UNITED STATES PATENT AND TRADEMARK OFFICE
CERTIFICATE OF CORRECTION

PATENT NO. : 4,977,177

DATED : December 11, 1990

INVENTOR(S) : Jerry C. Bommer, et al.

It is certified that error appears in the above-identified patent and that said Letters Patent is hereby corrected as shown below:

Column 14, line 26: "2.5'30" should read as --2.5 x 30--

Column 14, line 28: "(1 1 total" should read as --1 ℓ total--

Column 14, line 56: "1 5" should read as --1.5--

Column 14, line 62: "(1 1 total" should read as --(1 ℓ total--

Column 21, line 55: "qlycyl" should read as --glycyl--

Column 22, lines 7 & 38: "(1 1 total" should read as --(1 ℓ total--

Column 23, line 2: "(1 1 total" should read as --(1 ℓ total--

Column 23, line 17: "400 µg" should read as --400mg--

Column 23, line 34: "(1 1 total" should read as --(1 ℓ total--

Column 23, line 52: "36 ul" should read as --360ul--

Column 29, line 1: "of a" should read as --of an--

UNITED STATES PATENT AND TRADEMARK OFFICE
CERTIFICATE OF CORRECTION

PATENT NO. : 4,977,177

DATED : December 11, 1990

INVENTOR(S) : Jerry C. Bommer, et al.

It is certified that error appears in the above-identified patent and that said Letters Patent is hereby corrected as shown below:

Column 29, line 66, Claim 1: "-H" should read as -- -H;--

Column 30, line 68, Claim 24: "amide" should read as --amide is-- and delete "is' at the end of line Column 31, lines 2 & 4: "DL)" should read as --(DL)--

Column 32, lines 16 & 17: " $-CH_3;$ " should read as -- $-CH_3$ --
      $-OH;$       $-OH$ Column 32, line 38: "-H" should read as -- -H;--

Column 33, lines 36 & 37: " $-CH_3;$" should read as -- $-CH_3$ --
      $-OH;$       $-OH$ Column 34, lines 18 & 19: " $-CH_2CH_2CO_2H;$" should read as -- $-CH_2CH_2CO_2H$ "
      $-H$       $-H;$ Signed and Sealed this Twenty-fifth Day of August, 1992

*Attest:*

DOUGLAS B. COMER

*Attesting Officer*      *Acting Commissioner of Patents and Trademarks*